US010501701B2

(12) United States Patent
Salem et al.

(10) Patent No.: US 10,501,701 B2
(45) Date of Patent: *Dec. 10, 2019

(54) LUBRICATING COMPOSITION CONTAINING AN OXYALKYLATED AROMATIC POLYOL COMPOUND

(71) Applicant: The Lubrizol Corporation, Wickliffe, OH (US)

(72) Inventors: Kamalakumari Kunchithapatham Salem, Mentor, OH (US); David J. Moreton, Milford (GB); Mohamed G. Fahmy, Eastlake, OH (US); Gary M. Walker, Allestree (GB); James P. Roski, Mentor, OH (US); Yanshi Zhang, Solon, OH (US); Adam Cox, Novelty, OH (US); W. Preston Barnes, Chicago, IL (US); Ewan E. Delbridge, Concord Township, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 155 days.

This patent is subject to a terminal disclaimer.

(21) Appl. No.: 15/532,574

(22) PCT Filed: Dec. 3, 2015

(86) PCT No.: PCT/US2015/063701

§ 371 (c)(1),
(2) Date: Jun. 2, 2017

(87) PCT Pub. No.: WO2016/090121

PCT Pub. Date: Jun. 9, 2016

(65) Prior Publication Data

US 2017/0355924 A1 Dec. 14, 2017

Related U.S. Application Data

(60) Provisional application No. 62/086,831, filed on Dec. 3, 2014.

(51) Int. Cl.
*C07C 309/62* (2006.01)
*C10M 159/24* (2006.01)
(Continued)

(52) U.S. Cl.
CPC ........ *C10M 129/16* (2013.01); *C10M 129/20* (2013.01); *C10M 129/76* (2013.01); *C10M 139/00* (2013.01); *C10M 141/12* (2013.01); *C10M 169/048* (2013.01); *F02B 77/04* (2013.01); *C10M 2205/022* (2013.01); *C10M 2205/04* (2013.01); *C10M 2207/028* (2013.01); *C10M 2207/04* (2013.01); *C10M 2207/046* (2013.01); *C10M 2207/26* (2013.01); *C10M 2207/262* (2013.01); *C10M 2207/28* (2013.01); *C10M 2207/284* (2013.01); *C10M 2207/289* (2013.01); *C10M 2209/103* (2013.01); *C10M 2215/064* (2013.01); *C10M 2215/28* (2013.01); *C10M 2219/022* (2013.01); *C10M 2219/046* (2013.01); *C10M 2219/089* (2013.01); *C10M 2223/045* (2013.01); *C10M 2227/06* (2013.01); *C10N 2230/04* (2013.01); *C10N 2230/06* (2013.01); *C10N 2230/10* (2013.01); *C10N 2230/42* (2013.01); *C10N 2230/43* (2013.01); *C10N 2230/45* (2013.01); *C10N 2230/52* (2013.01); *C10N 2240/10* (2013.01); *C10N 2240/102* (2013.01); *C10N 2240/104* (2013.01)

(58) Field of Classification Search
CPC . C10M 129/91; C10M 129/10; C10M 129/16
USPC .................................................. 508/390, 392
See application file for complete search history.

(56) References Cited

U.S. PATENT DOCUMENTS 2,620,302 A 12/1952 Harle
2,620,304 A 12/1952 Stewart et al.
(Continued)

FOREIGN PATENT DOCUMENTS

EP 0796908 A1 9/1997
EP 2374866 A1 10/2011
(Continued)

*Primary Examiner* — Prem C Singh
*Assistant Examiner* — Francis C Campanell
(74) *Attorney, Agent, or Firm* — Christopher P. Demas; Teresan W. Gilbert

(57) ABSTRACT

The disclosed technology provides a lubricating composition comprising an oil of lubricating viscosity and 0.01 wt % to 10 wt % of an oxyalkylated aromatic polyol compound, wherein the aromatic compound has at least one alkoxy group represented by —$OR^1$ group, $R^1$ is hydroxyalkyl, or a (poly)ether group, and either: at least one hydroxyl group, or at least one alkoxy group represented by $OR^1$ group, where $R^1$ is alkyl, or a (poly)ether group, or at least one oxyalkyl group represented by —$OR^1$, where $R^1$ is hydroxyalkyl or a (poly)ether group. The disclosed technology further relates to a method of lubricating a mechanical device (such as an internal combustion engine) with the lubricating composition. The disclosed technology further relates to the use of the oxyalkylated aromatic polyol compound in the lubricating composition to a passenger car internal combustion engine at least one of (i) control of fuel economy, (ii) control of corrosion, (iii) cleanliness, and (iv) control of bore wear.

13 Claims, No Drawings

(51) Int. Cl.

| | |
|---|---|
| ***C10M 129/16*** | (2006.01) |
| ***C10M 169/04*** | (2006.01) |
| ***C10M 129/20*** | (2006.01) |
| ***C10M 129/76*** | (2006.01) |
| ***C10M 139/00*** | (2006.01) |
| ***C10M 141/12*** | (2006.01) |
| ***F02B 77/04*** | (2006.01) |

(56) References Cited

U.S. PATENT DOCUMENTS

| | | | | |
|---|---|---|---|---|
| 2,620,305 | A | 12/1952 | Stewart et al. | |
| 2,681,315 | A | 6/1954 | Tongberg | |
| 2,833,717 | A | 5/1958 | Whitacre | |
| 2,921,027 | A | 1/1960 | Brennan | |
| 3,933,662 | A | 1/1976 | Lowe | |
| 4,402,845 | A | 9/1983 | Zoleski et al. | |
| 4,438,005 | A | 3/1984 | Zoleski et al. | |
| 4,479,882 | A | 10/1984 | Zoleski et al. | |
| 4,493,776 | A | 1/1985 | Rhodes | |
| 4,973,414 | A | 11/1990 | Nerger et al. | |
| 9,868,919 | B2 | 1/2018 | Delbridge | |
| 2004/0077507 | A1 * | 4/2004 | Lange ................ | C08G 65/2612 508/199 |
| 2011/0239978 | A1 | 10/2011 | Dambacher et al. | |
| 2012/0135901 | A1 * | 5/2012 | Shaw .................. | C10M 169/04 508/460 |
| 2014/0011725 | A1 | 1/2014 | Marsh | |
| 2014/0130767 | A1 | 1/2014 | Marsh et al. | |
| 2014/0057819 | A1 | 2/2014 | Haensel | |
| 2015/0119306 | A1 | 4/2015 | Patil | |
| 2015/0119307 | A1 | 4/2015 | Patil | |
| 2017/0198233 | A1 * | 7/2017 | Zhang .................. | C10M 145/26 |

FOREIGN PATENT DOCUMENTS

| | | | |
|---|---|---|---|
| GB | 1127784 | A | 9/1968 |
| WO | 2014/164087 | A1 | 10/2014 |
| WO | 2014/193543 | A1 | 12/2014 |

* cited by examiner

LUBRICATING COMPOSITION CONTAINING AN OXYALKYLATED AROMATIC POLYOL COMPOUND

CROSS REFERENCE TO RELATED APPLICATION

This application claims priority from PCT Application Serial No. PCT/US2015/063701 filed on Dec. 3, 2015, which claims the benefit of U.S. Provisional Application No. 62/086,831 filed on Dec. 3, 2014, both of which are incorporated in their entirety by reference herein.

FIELD OF INVENTION

The disclosed technology provides lubricating composition comprising: an oil of lubricating viscosity, a lubricating composition comprising an oil of lubricating viscosity and 0.01 wt % to 10 wt % of an oxyalkylated aromatic polyol compound. The disclosed technology further relates to a method of lubricating a mechanical device (such as an internal combustion engine) with the lubricating composition. The disclosed technology further relates to the use of the oxyalkylated aromatic polyol compound in the lubricating composition for a passenger car internal combustion engine to control at least one of the following (i) fuel economy, (ii) corrosion, (iii) cleanliness, and (iv) bore wear.

BACKGROUND OF THE INVENTION

Detergents and dispersants are known to assist in maintaining reduced amounts of deposits on engine components. The lubricant industry has a number of engine tests used to evaluate lubricant's ability to handle deposits and sludge including the Sequence VG, Sequence IIIG, Volkswagen TDI, Caterpillar 1N, and Mercedes Benz OM501LA.

With recent changes to engine specifications there is an increasing demand on the lubricant to reduce deposits, especially soot deposits that are known to accumulate in diesel engines but not gasoline engines. For instance, the ILSAC GF-5 specification requires a 4.0 piston merit rating in the Sequence IIIG (vs. 3.5 for GF-4).

U.S. Pat. No. 3,933,662 (Lowe, published 20 Jan. 1976) discloses mono-ester polyalkoxylated compounds combined with alkaline earth metal carbonates dispersed in a hydrocarbon medium to provide lubricating compositions of superior acid neutralizing capability and rust inhibition in internal combustion engines. The internal combustion engine tested is a Sequence IIB gasoline engine. The Sequence IIB gasoline engine test evaluates valve guide rust and pitting.

US 2004/077507 (Lange et al., published 22 Apr. 2004) discloses an alkoxylated alkylphenol which have at least one long-chain alkyl radical having at least one tertiary or quaternary carbon atom are prepared and are used as fuel or lubricant additives in fuel and lubricant compositions. The alkoxylated alkylphenol may be useful for reducing sticking of valves and reducing the complete loss of compression on one or more cylinders of the internal combustion engine if-due to polymer deposits in the valve shaft-the spring forces are no longer sufficient to close the valves properly.

U.S. Pat. No. 4,402,845 (Zoleski et al., published 6 Sep. 1983) discloses improved spreadability of marine diesel cylinder oils by the incorporation therein of a polyethylene glycol of the formula: R—$CH_2O$—$(CH_2CH_2O)_n$H wherein n ranges from 7 to 40 and R is an alkyl group containing from 11 to 15 carbon atoms.

U.S. Pat. No. 4,438,005 (Zoleski et al., published 20 Mar. 1984) discloses improved spreadability of marine diesel engine cylinder lubricants by the incorporation therein of a spreadability improving amount of at least one polyoxyethylene ester of the formula disclosed therein: wherein n ranges from 18 to 22 and R is an alkyl group having 11 to 17 carbon atoms in the chain.

U.S. Pat. No. 4,479,882 (Zoleski et al., published 30 Oct. 1984) discloses improved spreadability of marine diesel cylinder oils by the incorporation therein of a spreadability improving amount of a polyethoxylated phenoxy compound having the formula disclosed therein: wherein R is an aliphatic hydrocarbyl group having from 5 to 70 carbon atoms and n ranges from 14 to 30.

U.S. Pat. No. 4,493,776 (Rhodes, published 15 Jan. 1985) discloses a lubricating composition with improved rust and corrosion inhibition comprising an additive that is a combination of (A) $R^1O[C_2H_4O]_xH$ and/or $R^2O[C_3H_6O]_yH$ with (B) $R^3O[C_2H_4O]_x[C_3H_6O]_yH$ and/or $R^4O[C_3H_6O]_y[C_2H_4O]_xH$, wherein $R^1$, $R^2$, $R^3$ and $R^4$ are hydrocarbyl radicals selected from alkyl, aryl, alkaryl, and arylalkyl groups or combinations thereof having from about 10 to about 24 carbon atoms; and wherein x and y may vary independently in the range from 3 to about 15. The additives are hydroxyl-terminated.

U.S. Pat. No. 4,973,414 (Nerger et al., published 27 Nov. 1990) discloses monofunctional polyethers having hydroxyl groups contain, as built-in terminal groups or monomers, (a) 1 to 30% by weight of one or more C4- to C24-alkylmonophenols, (b) 1 to 30% by weight of one or more C8- to C24-monoalkanols, (c) 1 to 30% by weight of one or more C10- to C20-1,2-epoxyalkanes and (d) 45 to 80% by weight of propylene oxide or a lower alkylene oxide mixture consisting mainly of propylene oxide the sum of components (a) to (d) adding up to 100% by weight, and have average molecular weights of 600 to 2,500.

Polyalkoxylated compounds are also disclosed in U.S. Pat. No. 2,681,315 (Tongberg, published 15 Jun. 1954) and U.S. Pat. No. 2,833,717 (Whitacre, published 6 May 1958) teaching lubricating oil compositions containing poly(oxyethylene)alkylphenols useful as rust or corrosion-inhibiting additives.

U.S. Pat. No. 2,921,027 (Brennan 12 Jan. 1960) teaches poly(oxyethylene)-sorbitan fatty acid ester as a rust inhibitor.

1,2-poly(oxyalkylene)glycol lubricating compositions are disclosed in U.S. Pat. No. 2,620,302 (Harle, published 2 Dec. 1952), U.S. Pat. No. 2,620,304 (Stewart et al., published 2 Dec. 1952), and U.S. Pat. No. 2,620,305 (Stewart et al., published 2 Dec. 1952).

US 2011/0239978 (Dambacher et al, published 6 Oct. 2011) discloses a lubricating composition that contains as an additive component, an oil-soluble mixture of oxyalkylated hydrocarbyl phenolcondensates wherein the oxyalkyl groups have the formula —(R'O)n- where R' is an ethylene, propylene or butylene group; and n is independently from 0 to 10; wherein less than 45 mole % of the phenolic functional groups of the condensates are non-oxyalkylated; and more than 55 mole % of the phenolic functional groups of the condensates are mono-oxyalkylated.

Research Disclosure RD 417045 (Anon, published 10 Jan. 1999) describes ethoxylated methylene-bridged alkyl phenols as detergents.

US 2014/130767 (Marsh et al., published 8 Jan. 2014) discloses an overbased sulfurised calcium phenate detergent additive, made from an aklylphenol, having oxyalkylated phenolic functional groups from unreacted alkylphenol starting material and lubricating compositions comprising the same.

International patent application WO/US2014/033323 (Zhang et al. filed 8 Apr. 2014) discloses a lubricating composition comprising: an oil of lubricating viscosity, and an oxyalkylated hydrocarbyl phenol, wherein the oxyalkylated hydrocarbyl phenol is substituted with at least one aliphatic hydrocarbyl group of 40 to 96 carbon atoms, and wherein the oxyalkylated hydrocarbyl phenol is substantially free of aromatic hydrocarbyl groups.

European Patent publication EP 2 374 866 A1 (published 12 Oct. 2011) relates to reducing deposits by employing a lubricating oil composition comprising (A) an oil of lubricating viscosity; and, (B) as an additive component, an oil-soluble mixture of oxyalkylated hydrocarbyl phenol condensates wherein the oxyalkyl groups have the formula —(R'O)n- where R' is an ethylene, a propylene or a butylene group; n is independently from 0 to 10; less than 45 mole % of the phenolic hydroxyl groups in the mixture are not oxyalkylated; and more than 55 mole % of the oxyalkyl groups in the mixture have the formula —R'O— where n is 1.

SUMMARY OF THE INVENTION

The objectives of the disclosed technology include providing a lubricating composition for a passenger car internal combustion engine, typically a diesel passenger car internal combustion engine, to control at least one of the following (i) fuel economy, (ii) corrosion, (iii) cleanliness, and (iv) bore wear.

As used herein, reference to the amounts of additives present in the lubricating composition disclosed are quoted on an oil free basis, i.e., amount of actives, unless otherwise indicated.

As used herein, the transitional term "comprising", which is synonymous with "including", "containing", or "characterized by", is inclusive or open-ended and does not exclude additional, un-recited elements or method steps. However, in each recitation of "comprising" herein, it is intended that the term also encompass, as alternative embodiments, the phrases "consisting essentially of" and "consisting of", where "consisting of" excludes any element or step not specified and "consisting essentially of" permits the inclusion of additional un-recited elements or steps that do not materially affect the basic and novel, and essential characteristics of the composition or method under consideration.

As used herein the term "aromatic polyol compound" is intended to include substituted and unsubstituted compounds that have two or more hydroxyl groups directly bonded to an aromatic group (within the definition of Hückel Rule 4π+2 electrons) such as catechol, or pyrrogallol.

In one embodiment the disclosed technology provides a lubricating composition comprising an oil of lubricating viscosity and 0.01 wt % to 10 wt % of an oxyalkylated aromatic polyol compound, wherein the aromatic compound has at least one oxyalkyl group represented by —$OR^1$ group, $R^1$ is hydroxyhydroxyalkyl, or a (poly)ether group, and:

at least one hydroxyl group, or at least one alkoxy group represented by —$OR^1$ group, where $R^1$ is alkyl, or a (poly)ether group, or at least one oxyalkyl group represented by —$OR^1$, where $R^1$ is hydroxyalkyl or a (poly)ether group.

In one embodiment the disclosed technology provides a lubricating composition comprising: an oil of lubricating viscosity, and an oxyalkylated aromatic polyol compound, wherein the oxyalkylated aromatic polyol compound is further substituted with at least one aliphatic hydrocarbyl group of 1 to 150 carbon atoms (or 1 to 80, 10 to 40, or 30 to 100, or 40 to 96 carbon atoms), or a hydrocarbyl group containing 6 to 36, 10 to 30 or 12 to 24 carbon atoms. The oxyalkylated aromatic polyol compound may be substantially free of aromatic hydrocarbyl groups.

The oxyalkylated aromatic polyol compound may be represented by the formula:

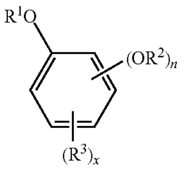

wherein $R^1$ may be —$(CH_2CHR^5$—O—$)_mR^6$, $R^2$ may be hydrogen, a hydrocarbyl group (typically containing 1 to 24, or 1 to 12, carbon atoms), or —(C=O)$R^4$, —$(CH_2CHR^5$—O—$)_mR^6$, n may be 1 or 2, $R^3$ may be a hydrocarbyl group (typically containing 1 to 150 carbon atoms (or 1 to 80, 10 to 40, or 30 to 100, or 40 to 96 carbon atoms, or a hydrocarbyl group containing 6 to 36, 10 to 30 or 12 to 24 carbon atoms, —(C=O)$OR^4$, or —$(CH_2CHR^5$—O—$)_mR^6$, x may be 0 to 2, $R^4$ may be a hydrocarbyl group (typically containing 1 to 24, or 1 to 12 carbon atoms), $R^5$ may be hydrogen or a hydrocarbyl group containing 1 to 32, or 1 to 24, or 1 to 16, or 2 to 16, or 8 to 16, or 1 to 4, (or 1 to 2) carbon atoms, or $CH_2OR^8$, $R^6$ may be hydrogen or a hydrocarbyl group (typically containing 1 to 24, or 1 to 12 carbon atoms), —(C=O)$R^7$, $R^7$ may be a hydrocarbyl group (typically containing 1 to 24, or 1 to 12, carbon atoms), $R^8$ may be hydrogen or a hydrocarbyl group containing 1 to 24, or 4 to 20, or 10 to 18 carbon atoms, and m=1 to 20 or 5 to 18.

When n=2, each $R^2$ may be taken together to form a 5-membered or 6-membered ring.

In one embodiment n=1 and x=1.

In one embodiment n=2 and x=1.

When $R^3$ has 30 to 100, or 40 to 96 carbon atoms it may be a polyisobutenyl or polyisobutylene group. The $R^3$ group may for example have a number average molecular weight of polyisobutylene of 550, or 750, or 950.

When $R^3$ has 6 to 36, 10 to 30 or 12 to 24 carbon atoms it may be an olefin group. The olefin may include decene, dodecene, tetradecene, hexadecene, octadecene, eicosene, doeicosene, tetraeicosene, hexaeicosene or octaeicosene, or mixtures thereof.

The olefin may be a mixture of 15 to 18, or 16 to 18, or 16 to 22, or 20 to 28, or 20 to 24 carbon atoms. In one embodiment the olefin may be a mixture of 20 to 24 carbon atoms.

In one embodiment the olefin may be dodecene.

The oxyalkylated aromatic polyol compound may be represented by the formula:

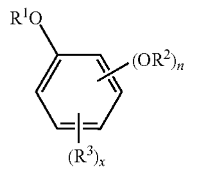

wherein $R^1$ may be —$(CH_2CHR^5$—O—$)_mR^6$, $R^2$ may be hydrogen, a hydrocarbyl group (typically containing 1 to 24, or 1 to 12, carbon atoms), or —(C═O)$R^4$, —$(CH_2CHR^5$—O—$)_mR^6$, n may be 1 or 2, $R^3$ may be a polyisobutenyl or polyisobutylene group typically having 30 to 100, or 40 to 96 carbon atoms, x may be 0 to 2, $R^4$ may be a hydrocarbyl group (typically containing 1 to 24, or 1 to 12 carbon atoms), $R^5$ may be hydrogen or a hydrocarbyl group containing 1 to 32, or 1 to 24, or 1 to 16, or 2 to 16, or 8 to 16, or 1 to 4, (or 1 to 2) carbon atoms, or $CH_2OR^8$, $R^6$ may be hydrogen or a hydrocarbyl group (typically containing 1 to 24, or 1 to 12 carbon atoms), —(C═O)$R^7$, $R^7$ may be a hydrocarbyl group (typically containing 1 to 24, or 1 to 12, carbon atoms), $R^8$ may be hydrogen or a hydrocarbyl group containing 1 to 24, or 4 to 20, or 10 to 18 carbon atoms, and m=1 to 20 or 5 to 18.

When n=2, each $R^2$ may be taken together to form a 5-membered or 6-membered ring.

The oxyalkylated aromatic polyol compound may be represented by the formula:

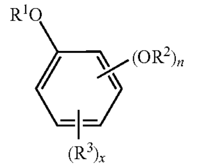

wherein $R^1$ may be —$(CH_2CHR^5$—O—$)_mR^6$, $R^2$ may be hydrogen, a hydrocarbyl group (typically containing 1 to 24, or 1 to 12, carbon atoms), or —(C═O)$R^4$, —$(CH_2CHR^5$—O—$)_mR^6$, n may be 1 or 2, $R^3$ may be an olefin group having 6 to 36, 10 to 30 or 12 to 24 carbon atoms, x may be 0 to 2, $R^4$ may be a hydrocarbyl group (typically containing 1 to 24, or 1 to 12 carbon atoms), $R^5$ may be hydrogen or a hydrocarbyl group containing 1 to 32, or 1 to 24, or 1 to 16, or 2 to 16, or 8 to 16, or 1 to 4, (or 1 to 2) carbon atoms, or $CH_2OR^8$, $R^6$ may be hydrogen or a hydrocarbyl group (typically containing 1 to 24, or 1 to 12 carbon atoms), —(C═O)$R^7$, $R^7$ may be a hydrocarbyl group (typically containing 1 to 24, or 1 to 12, carbon atoms), $R^8$ may be hydrogen or a hydrocarbyl group containing 1 to 24, or 4 to 20, or 10 to 18 carbon atoms, and m=1 to 20 or 5 to 18.

When n=2, each $R^2$ may be taken together to form a 5-membered or 6-membered ring.

In one embodiment the disclosed technology provides a lubricating composition characterised as having at least one of (i) a sulfur content of 0.2 wt % to 0.4 wt % or less, (ii) a phosphorus content of 0.08 wt % to 0.15 wt %, and (iii) a sulphated ash content of 0.5 wt % to 1.5 wt % or less.

In one embodiment the disclosed technology provides a lubricating composition characterised as having (i) a sulfur content of 0.5 wt % or less, (ii) a phosphorus content of 0.1 wt % or less, and (iii) a sulphated ash content of 0.5 wt % to 1.5 wt % or less.

The lubricant may have a SAE viscosity grade of XW—Y, wherein X may be 0, 5, 10, or 15; and Y may be 16, 20, 30, or 40.

The oil of lubricating viscosity may comprise an API Group I, II, III, IV, V, or mixtures thereof base oil.

The lubricating composition disclosed herein may comprise 0 wt % to 0.2, or 0.01 to 0.1 wt % of an overbased calcium sulfonate detergent.

The lubricating composition disclosed herein may comprise 0.5 wt % to 3 wt %, or 0.9 wt % to 2 wt % of calcium phenate detergent (typically overbased).

In one embodiment the lubricating composition disclosed herein may comprise 0.5 wt % to 3 wt %, or 0.9 wt % to 2 wt % of calcium phenate detergent (typically overbased), and 0 wt % to 0.2, or 0.01 to 0.1 wt % of an overbased calcium sulfonate detergent.

In one embodiment the disclosed technology provides a method of lubricating an internal combustion engine comprising supplying to the internal combustion engine a lubricating composition of a lubricating disclosed herein.

The internal combustion engine may have a steel surface on a cylinder bore, a cylinder block, or a piston ring.

The internal combustion engine may be a heavy duty diesel internal combustion engine.

The heavy duty diesel internal combustion engine may have a "technically permissible maximum laden mass" over 3,500 kg. The engine may be a compression ignition engine or a positive ignition natural gas (NG) or LPG (liquefied petroleum gas) engine. The internal combustion engine may be a passenger car internal combustion engine. The passenger car engine may be operated on unleaded gasoline. Unleaded gasoline is well known in the art and is defined by British Standard BS EN 228:2008 (entitled "Automotive Fuels—Unleaded Petrol—Requirements and Test Methods").

The passenger car internal combustion engine may have a reference mass not exceeding 2610 kg. The passenger car internal combustion engine may be gasoline or diesel.

The disclosed technology may also provide for a method of controlling soot formation in a 4-stroke compression ignition engine or a positive ignition natural gas (NG) or LPG engine comprising supplying to the engine a lubricating composition disclosed herein.

In one embodiment the disclosed technology provides for the use of the oxyalkylated aromatic polyol compound disclosed herein in a lubricating composition provide at least one of (i) control of fuel economy, (ii) control of corrosion, (iii) cleanliness (typically control of deposits, typically control/reduction of soot), and (iv) control of bore wear in an internal combustion engine. Typically the internal combustion engine may be a diesel passenger car internal combustion engine.

In one embodiment the disclosed technology provides for the use of the oxyalkylated aromatic polyol compound disclosed herein in a lubricating composition for a diesel passenger car internal combustion engine to control soot deposit formation.

DETAILED DESCRIPTION OF THE INVENTION

The disclosed technology provides a lubricating composition, a method for lubricating an internal combustion engine and the use as disclosed above.

Oxyalkylated Aromatic Polyol Compound

The oxyalkylated aromatic polyol compound may be represented by the formula:

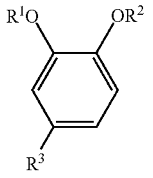

wherein $R^1$ may be —$(CH_2CHR^5$—O—$)_mR^6$, $R^2$ may be hydrogen, $R^3$ may be a hydrocarbyl group (typically containing 1 to 150 carbon atoms (or 1 to 80, 10 to 40, or 30 to 100, or 40 to 96 carbon atoms) or a hydrocarbyl group containing 6 to 36, 10 to 30 or 12 to 24 carbon atoms, or C(═O)$OR^4$, $R^4$ may be a hydrocarbyl group (typically containing 1 to 24, or 1 to 12 carbon atoms), $R^5$ may be hydrogen or a hydrocarbyl group containing 1 to 32, or 1 to 24, or 1 to 16, or 2 to 16, or 8 to 16, or 1 to 4, (or 1 to 2) carbon atoms, or $CH_2OR^8$, $R^6$ may be hydrogen or a hydrocarbyl group (typically containing 1 to 24, or 1 to 12 carbon atoms), $R^8$ may be hydrogen or a hydrocarbyl group containing 1 to 24, or 4 to 20, or 10 to 18 carbon atoms, and m=1 to 20, or 5 to 18.

The oxyalkylated aromatic polyol compound may be represented by the formula:

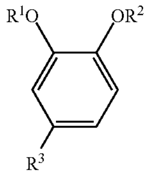

wherein $R^1$ may be —$(CH_2CHR^5$—O—$)_mR^6$, $R^2$ may be —$(CH_2CHR^5$—O—$)_mR^6$, $R^3$ may be a hydrocarbyl group (typically containing 1 to 150 carbon atoms (or 1 to 80, 10 to 40, or 30 to 100, or 40 to 96 carbon atoms) or a hydrocarbyl group containing 6 to 36, 10 to 30 or 12 to 24 carbon atoms, or C(═O)$OR^4$,$R^4$ may be a hydrocarbyl group (typically containing 1 to 24, or 1 to 12 carbon atoms), $R^5$ may be hydrogen or a hydrocarbyl group containing 1 to 32, or 1 to 24, or 1 to 16, or 2 to 16, or 8 to 16, or 1 to 4, (or 1 to 2) carbon atoms, or $CH_2OR^8$, $R^6$ may be hydrogen or a hydrocarbyl group (typically containing 1 to 24, or 1 to 12 carbon atoms), $R^8$ may be hydrogen or a hydrocarbyl group containing 1 to 24, or 4 to 20, or 10 to 18 carbon atoms, and m=1 to 20, or 5 to 18.

The oxyalkylated aromatic polyol compound may be represented by the formula:

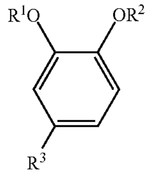

wherein $R^1$ may be —$(CH_2CHR^5$—O—$)_mR^6$, $R^2$ may be a hydrocarbyl group (typically containing 1 to 24, or 1 to 12, carbon atoms), or —$(CH_2CHR^5$—O—$)_mR^6$, $R^3$ may be a hydrocarbyl group (typically containing 1 to 150 carbon atoms (or 1 to 80, 10 to 40, or 30 to 100, or 40 to 96 carbon atoms) or a hydrocarbyl group containing 6 to 36, 10 to 30 or 12 to 24 carbon atoms, or C(═O)$OR^4$, $R^4$ may be a hydrocarbyl group (typically containing 1 to 24, or 1 to 12 carbon atoms), $R^5$ may be hydrogen or a hydrocarbyl group containing 1 to 32, or 1 to 24, or 1 to 16, or 2 to 16, or 8 to 16, or 1 to 4, (or 1 to 2) carbon atoms, or $CH_2OR^8$, $R^6$ may be hydrogen or a hydrocarbyl group (typically containing 1 to 24, or 1 to 12 carbon atoms), $R^8$ may be hydrogen or a hydrocarbyl group containing 1 to 24, or 4 to 20, or 10 to 18 carbon atoms, and m=1 to 20, or 5 to 18.

The oxyalkylated aromatic polyol compound may be represented by the formula:

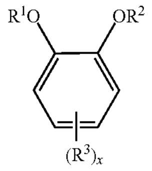

wherein $R^1$ may be —$(CH_2CHR^5$—O—$)_mR^6$, $R^2$ may be hydrogen, $R^3$ may be a hydrocarbyl group (typically containing 1 to 150 carbon atoms (or 1 to 80, 10 to 40, or 30 to 100, or 40 to 96 carbon atoms) or a hydrocarbyl group containing 6 to 36, 10 to 30 or 12 to 24 carbon atoms, or C(═O)$OR^4$, x=2, $R^4$ may be a hydrocarbyl group (typically containing 1 to 24, or 1 to 12 carbon atoms), $R^5$ may be hydrogen or a hydrocarbyl group containing 1 to 32, or 1 to 24, or 1 to 16, or 2 to 16, or 8 to 16, or 1 to 4, (or 1 to 2) carbon atoms, or $CH_2OR^8$, $R^6$ may be hydrogen or a hydrocarbyl group (typically containing 1 to 24, or 1 to 12 carbon atoms), $R^8$ may be hydrogen or a hydrocarbyl group containing 1 to 24, or 4 to 20, or 10 to 18 carbon atoms, and m=1 to 20, or 5 to 18.

The oxyalkylated aromatic polyol compound (may be from pyrogallol) may be represented by the formula:

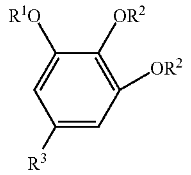

wherein $R^1$ may be $—(CH_2CHR^5—O—)_mR^6$, $R^2$ and $R^3$ may be independently hydrogen, a hydrocarbyl group (typically containing 1 to 150 carbon atoms (or 1 to 80, 10 to 40, or 30 to 100, or 40 to 96 carbon atoms) or a hydrocarbyl group containing 6 to 36, 10 to 30 or 12 to 24 carbon atoms, or $R^3$ may be $C(=O)OR^4$, $R^4$ may be a hydrocarbyl group (typically containing 1 to 24, or 1 to 12 carbon atoms), $R^5$ may be hydrogen or a hydrocarbyl group containing 1 to 32, or 1 to 24, or 1 to 16, or 2 to 16, or 8 to 16, or 1 to 4, (or 1 to 2) carbon atoms, or $CH_2OR^8$, $R^6$ may be hydrogen or a hydrocarbyl group (typically containing 1 to 24, or 1 to 12 carbon atoms), $R^8$ may be hydrogen or a hydrocarbyl group containing 1 to 24, or 4 to 20, or 10 to 18 carbon atoms, and m=1 to 20, or 5 to 18.

The oxyalkylated aromatic polyol compound (may be from pyrogallol) may be represented by the formula:

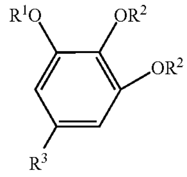

wherein $R^1$ may be $—(CH_2CHR^5—O—)_mR^6$, $R^2$ may be hydrogen, $R^3$ may be a hydrocarbyl group (typically containing 1 to 150 carbon atoms (or 1 to 80, 10 to 40, or 30 to 100, or 40 to 96 carbon atoms), or a hydrocarbyl group containing 6 to 36, 10 to 30 or 12 to 24 carbon atoms, or $C(=O)OR^4$, $R^4$ may be a hydrocarbyl group (typically containing 1 to 24, or 1 to 12 carbon atoms), $R^5$ may be hydrogen or a hydrocarbyl group containing 1 to 32, or 1 to 24, or 1 to 16, or 2 to 16, or 8 to 16, or 1 to 4, (or 1 to 2) carbon atoms, or $CH_2OR^8$, $R^6$ may be hydrogen or a hydrocarbyl group (typically containing 1 to 24, or 1 to 12 carbon atoms), $R^8$ may be hydrogen or a hydrocarbyl group containing 1 to 24, or 4 to 20, or 10 to 18 carbon atoms, and m=1 to 20, or 5 to 18.

For the pyrogallol based oxyalkylated aromatic polyol compound the $—OR^1$ and $—OR^2$ groups may be exchanged on the formula shown above. A person skilled in the art would realize that the alkoxylation of pyrogallol can occur on any of the three hydroxyl groups.

The oxyalkylated aromatic polyol compound may be prepared by reacting an oxyalkylated aromatic polyol compound with an alkylene oxide (typically ethylene oxide, propylene oxide or butylene oxide), optionally in the presence of a base catalyst. Typically the reaction occurs in the presence of a base catalyst.

The base catalyst may include sodium chloroacetate, sodium hydride sodium hydroxide, or potassium hydroxide.

The hydrocarbyl group (also represented by $R^3$) may be linear or branched, typically with at least one branching point. The aliphatic hydrocarbyl group typically has one, although it may in some embodiments be desirable to have to $R^3$ groups.

In different embodiments the oxyalkylated aromatic polyol compound of the disclosed technology may be present in an amount ranging from 0.01 wt % to 5 wt %, or 0.05 to 3 wt %, or 0.1 to 1.5 wt % of the lubricating composition. Typically the oxyalkylated aromatic polyol compound may be present in an amount from 0.1 to 1.5 wt % of the lubricating composition.

Oils of Lubricating Viscosity

The lubricating composition comprises an oil of lubricating viscosity. Such oils include natural and synthetic oils, oil derived from hydrocracking, hydrogenation, and hydrofinishing, unrefined, refined and re-refined oils and mixtures thereof.

Unrefined oils are those obtained directly from a natural or synthetic source generally without (or with little) further purification treatment.

Refined oils are similar to the unrefined oils except they have been further treated in one or more purification steps to improve one or more properties. Purification techniques are known in the art and include solvent extraction, secondary distillation, acid or base extraction, filtration, percolation and the like.

Re-refined oils are also known as reclaimed or reprocessed oils, and are obtained by processes similar to those used to obtain refined oils and often are additionally processed by techniques directed to removal of spent additives and oil breakdown products.

Natural oils useful in making the inventive lubricants include animal oils, vegetable oils (e.g., castor oil,), mineral lubricating oils such as liquid petroleum oils and solvent-treated or acid-treated mineral lubricating oils of the paraffinic, naphthenic or mixed paraffinic-naphthenic types and oils derived from coal or shale or mixtures thereof.

Synthetic lubricating oils are useful and include hydrocarbon oils such as polymerised and interpolymerised olefins (e.g., polybutylenes, polypropylenes, propyleneisobutylene copolymers); poly(1-hexenes), poly(1-octenes), poly(1-decenes), and mixtures thereof; alkyl-benzenes (e.g. dodecylbenzenes, tetradecylbenzenes, dinonylbenzenes, di-(2-ethylhexyl)-benzenes); polyphenyls (e.g., biphenyls, terphenyls, alkylated polyphenyls); diphenyl alkanes, alkylated diphenyl alkanes, alkylated diphenyl ethers and alkylated diphenyl sulfides and the derivatives, analogs and homologs thereof or mixtures thereof.

Other synthetic lubricating oils include polyol esters (such as Priolube®3970), diesters, liquid esters of phosphorus-containing acids (e.g., tricresyl phosphate, trioctyl phosphate, and the diethyl ester of decane phosphonic acid), or polymeric tetrahydrofurans. Synthetic oils may be produced by Fischer-Tropsch reactions and typically may be hydroisomerised Fischer-Tropsch hydrocarbons or waxes. In one embodiment oils may be prepared by a Fischer-Tropsch gas-to-liquid synthetic procedure as well as other gas-to-liquid oils.

Oils of lubricating viscosity may also be defined as specified in the American Petroleum Institute (API) Base Oil Interchangeability Guidelines. The five base oil groups are as follows: Group I (sulfur content >0.03 wt %, and/or <90 wt % saturates, viscosity index 80-120); Group II (sulfur content ≤0.03 wt %, and ≥90 wt % saturates, viscosity index 80-120); Group III (sulfur content ≤0.03 wt %, and ≥90 wt % saturates, viscosity index ≥120); Group IV (all polyalphaolefins (PAOs)); and Group V (all others not included in Groups I, II, III, or IV). The oil of lubricating viscosity may also be an API Group II+ base oil, which term refers to a Group II base oil having a viscosity index greater than or equal to 110 and less than 120, as described in SAE publication "Design Practice: Passenger Car Automatic Transmissions", fourth Edition, AE-29, 2012, page 12-9, as well as in U.S. Pat. No. 8,216,448, column 1 line 57.

The oil of lubricating viscosity may be an API Group IV oil, or mixtures thereof, i.e., a polyalphaolefin. The polyalphaolefin may be prepared by metallocene catalyzed processes or from a non-metallocene process.

The oil of lubricating viscosity comprises an API Group I, Group II, Group III, Group IV, Group V oil or mixtures thereof.

Often the oil of lubricating viscosity may be an API Group I, Group II, Group II+, Group III, Group IV oil or mixtures thereof. Alternatively the oil of lubricating viscosity may be often an API Group II, Group II+, Group III or Group IV oil or mixtures thereof. Alternatively the oil of lubricating viscosity may be often an API Group II, Group II+, Group III oil or mixtures thereof.

The amount of the oil of lubricating viscosity present may be typically the balance remaining after subtracting from 100 wt % the sum of the amount of the additive as described herein above, and the other performance additives.

The lubricating composition may be in the form of a concentrate and/or a fully formulated lubricant. If the lubricating composition of the disclosed technology is in the form of a concentrate (which may be combined with additional oil to form, in whole or in part, a finished lubricant), the ratio of the of components of the disclosed technology to the oil of lubricating viscosity and/or to diluent oil include the ranges of 1:99 to 99:1 by weight, or 80:20 to 10:90 by weight.

Other Performance Additives

A lubricating composition may be prepared by adding the oxyalkylated aromatic polyol compound described herein to an oil of lubricating viscosity, optionally in the presence of other performance additives (as described herein below).

The lubricating composition of the disclosed technology may further include other additives. In one embodiment the disclosed technology provides a lubricating composition further comprising at least one of a dispersant, an antiwear agent, a dispersant viscosity modifier, a friction modifier, a viscosity modifier, an antioxidant, an overbased detergent, a foam inhibitor, a demulsifier, a pour point depressant or mixtures thereof. In one embodiment the disclosed technology provides a lubricating composition further comprising at least one of a polyisobutylene succinimide dispersant, an antiwear agent, a dispersant viscosity modifier, a friction modifier, a viscosity modifier (typically an olefin copolymer such as an ethylene-propylene copolymer), an antioxidant (including phenolic and aminic antioxidants), an overbased detergent (including overbased sulfonates and phenates), or mixtures thereof.

The lubricating composition disclosed herein may further comprise an overbased detergent. The overbased detergent may be chosen from of non-sulfur containing phenates, sulfur containing phenates, sulfonates, salixarates, salicylates, and mixtures thereof. In one embodiment the overbased detergent may be chosen from of non-sulfur containing phenates, sulfur containing phenates, sulfonates and mixtures thereof.

Typically an overbased detergent may be sodium, calcium or magnesium (typically calcium) salt of the phenates, sulfur containing phenates, sulfonates, salixarates and salicylates. Overbased phenates and salicylates typically have a total base number of 180 to 450 TBN. Overbased sulfonates typically have a total base number of 250 to 600, or 300 to 500. Overbased detergents are known in the art. In one embodiment the sulfonate detergent may be a predominantly linear alkylbenzene sulfonate detergent having a metal ratio of at least 8 as is described in US Patent Application 2005/065045 (and granted as U.S. Pat. No. 7,407,919). Linear alkyl benzenes may have the benzene ring attached anywhere on the linear chain, usually at the 2, 3, or 4 position, or mixtures thereof. The predominantly linear alkylbenzene sulfonate detergent may be particularly useful for assisting in improving fuel economy. In one embodiment, the sulfonate detergent may be a branched alkylbenzene sulfonate detergent. Branched alkylbenzene sulfonate may be prepared from isomerized alpha olefins, oligomers of low molecular weight olefins, or combinations thereof. Typical oligomers include tetramers, pentamers, and hexamers of propylene and butylene. In one embodiment the sulfonate detergent may be a metal salt of one or more oil-soluble alkyl toluene sulfonate compounds as disclosed in US Patent Application 2008/0119378.

The overbased metal-containing detergent may also include “hybrid” detergents formed with mixed surfactant systems including phenate and/or sulfonate components, e.g., phenate/salicylates, sulfonate/phenates, sulfonate/salicylates, sulfonates/phenates/salicylates, as described; for example, in U.S. Pat. Nos. 6,429,178; 6,429,179; 6,153,565; and 6,281,179. Where, for example, a hybrid sulfonate/phenate detergent may be employed, the hybrid detergent would be considered equivalent to amounts of distinct phenate and sulfonate detergents introducing like amounts of phenate and sulfonate soaps, respectively.

Lubricating compositions may contain phenol-based detergents, i.e. detergents wherein the substrate includes or may be derived from phenol or alkylphenol. Detergents of this type include sulfur-coupled phenates, alkylene-coupled phenates, salicylates (i.e. carboxylated phenol), salixarates, and saligenins These phenol-based detergents may be neutral or overbased.

In one embodiment the lubricating composition further comprises a non-sulfur containing phenate, or sulfur containing phenate, or mixtures thereof. The non-sulfur containing phenates and sulfur containing phenates and known in the art. The non-sulfur containing phenate, or sulfur containing phenate may be neutral or overbased. Typically an overbased non-sulfur containing phenate, or a sulfur containing phenate have a total base number of 180 to 450 TBN and a metal ratio of 2 to 15, or 3 to 10. A neutral non-sulfur containing phenate, or sulfur containing phenate may have a TBN of 80 to less than 180 and a metal ratio of 1 to less than 2, or 0.05 to less than 2.

The non-sulfur containing phenate, or sulfur containing phenate may be in the form of a calcium or magnesium non-sulfur containing phenate, or sulfur containing phenate (typically calcium non-sulfur containing phenate, or sulfur containing phenate). When present the non-sulfur containing phenate, or sulfur containing phenate may be present at 0.1 to 10 wt %, or 0.5 to 8 wt %, or 1 to 6 wt %, or 2.5 to 5.5 wt % of the lubricating composition.

In one embodiment the lubricating composition may be free of an overbased phenate, and in a different embodiment the lubricating composition may be free of a non-overbased phenate. In another embodiment the lubricating composition may be free of a phenate detergent.

Phenate detergents are typically derived from p-hydrocarbyl phenols. Alkylphenols of this type may be coupled with sulfur and overbased, coupled with aldehyde and overbased, or carboxylated to form salicylate detergents. Suitable alkylphenols include those alkylated with oligomers of propylene, i.e. tetrapropenylphenol (i.e. p-dodecylphenol or PDDP) and pentapropenylphenol. Suitable alkylphenols also include those alkylated with oligomers of butene, especially tetramers and pentamers of n-butenes. Other suitable alkylphenols include those alkylated with alpha-olefins, isomerized alpha-olefins, and polyolefins like polyisobutylene. In one embodiment, the lubricating composition comprises less than 0.2 wt %, or less than 0.1 wt %, or even less than 0.05 wt % of a phenate detergent derived from PDDP. In one embodiment, the lubricant composition comprises a phenate detergent that is not derived from PDDP. In one embodiment, the lubricating composition comprises a phenate detergent prepared from PDDP wherein the phenate detergent contains less than 1.0 weight percent unreacted PDDP, or less than 0.5 weight percent unreacted PDDP, or substantially free of PDDP.

In one embodiment the lubricating composition further comprises a salicylate detergent that may be neutral or overbased. The salicylates and known in the art. The salicylate detergent may have a TBN of 50 to 400, or 150 to 350, and a metal ratio of 0.5 to 10, or 0.6 to 2. Suitable salicylate detergents included alkylated salicylic acid, or alkylsalicylic acid. Alkylsalicylic acid may be prepared by alkylation of salicylic acid or by carbonylation of alkylphenol. When alkylsalicylic acid may be prepared from alkylphenol, the alkylphenol may be selected in a similar manner as the phenates described above. In one embodiment, alkylsalicylate of the disclosed technology include those alkylated with oligomers of propylene, i.e. tetrapropenylphenol (i.e. p-dodecylphenol or PDDP) and pentapropenylphenol. Suitable alkylphenols also include those alkylated with oligomers of butane, especially tetramers and pentamers of n-butenes. Other suitable alkylphenols include those alkylated with alpha-olefins, isomerized alpha-olefins, and polyolefins like polyisobutylene. In one embodiment, the lubricating composition comprises a salicylate detergent prepared from PDDP wherein the phenate detergent contains less than 1.0 weight percent unreacted PDDP, or less than 0.5 weight percent unreacted PDDP, or substantially free of PDDP.

When present the salicylate may be present at 0.01 to 10 wt %, or 0.1 to 6 wt %, or 0.2 to 5 wt %, 0.5 to 4 wt %, or 1 to 3 wt % of the lubricating composition.

Overbased detergents are known in the art. Overbased materials, otherwise referred to as overbased or superbased salts, are generally single phase, homogeneous Newtonian systems characterised by a metal content in excess of that which would be present for neutralization according to the stoichiometry of the metal and the particular acidic organic compound reacted with the metal. The overbased materials are prepared by reacting an acidic material (typically an inorganic acid or lower carboxylic acid, typically carbon dioxide) with a mixture comprising an acidic organic compound, a reaction medium comprising at least one inert, organic solvent (mineral oil, naphtha, toluene, xylene, etc.) for said acidic organic material, a stoichiometric excess of a metal base, and a promoter such as a calcium chloride, acetic acid, phenol or alcohol. The acidic organic material will normally have a sufficient number of carbon atoms to provide a degree of solubility in oil. The amount of "excess" metal (stoichiometrically) may be commonly expressed in terms of metal ratio. The term "metal ratio" is the ratio of the total equivalents of the metal to the equivalents of the acidic organic compound. A neutral metal salt has a metal ratio of one. A salt having 4.5 times as much metal as present in a normal salt will have metal excess of 3.5 equivalents, or a ratio of 4.5. The term "metal ratio" is also explained in standard textbook entitled "Chemistry and Technology of Lubricants", Third Edition, Edited by R. M. Mortier and S. T. Orszulik, Copyright 2010, page 219, sub-heading 7.25.

The overbased detergent may be present at 0.1 wt % to 10 wt %, or 0.2 wt % to 8 wt %, or 0.2 wt % to 3 wt %. For example in a heavy duty diesel engine the detergent may be present at 2 wt % to 3 wt % of the lubricating composition. For a passenger car engine the detergent may be present at 0.2 wt % to 1 wt % of the lubricating composition. In one embodiment, an engine lubricating composition comprises at least one overbased detergent with a metal ratio of at least 3, or at least 8, or at least 15. In one embodiment, the overbased detergent may be present in an amount to deliver total base number (TBN) of at least 3 mg KOH/g to the lubricating composition or at least 4 mg KOH/g, or at least 5 mg KOH/g to the lubricating composition; the overbased detergent may deliver 3 to 10 mg KOH/g, or 5 to 10 mg KOH/g to the lubricating composition.

As referred to herein, the TBN may be measured using ASTM D2986-11.

The lubricating composition may further include a dispersant, or mixtures thereof. The dispersant may be a succinimide dispersant, a Mannich dispersant, a succinamide dispersant, a polyolefin succinic acid ester, amide, or ester-amide, or mixtures thereof. In one embodiment the disclosed technology does include a dispersant or mixtures thereof. The dispersant may be present as a single dispersant. The dispersant may be present as a mixture of two or more (typically two or three) different dispersants, wherein at least one may be a succinimide dispersant.

The succinimide dispersant may be derived from an aliphatic polyamine, or mixtures thereof. The aliphatic polyamine may be aliphatic polyamine such as an ethylenepolyamine, a propylenepolyamine, a butylenepolyamine, or mixtures thereof. In one embodiment the aliphatic polyamine may be ethylenepolyamine. In one embodiment the aliphatic polyamine may be chosen from of ethylenediamine, diethylenetriamine, triethylenetetramine, tetraethylenepentamine, pentaethylene-hexamine, polyamine still bottoms, and mixtures thereof.

The succinimide dispersant may be a derivative of an aromatic amine, an aromatic polyamine, or mixtures thereof. The aromatic amine may be 4-aminodiphenylamine (ADPA) (also known as N-phenylphenylenediamine), derivatives of ADPA (as described in United States Patent Publications 2011/0306528 and 2010/0298185), a nitroaniline, an aminocarbazole, an amino-indazolinone, an aminopyrimidine, 4-(4-nitrophenylazo)aniline, or combinations thereof. In one embodiment, the dispersant may be derivative of an aromatic amine wherein the aromatic amine has at least three non-continuous aromatic rings.

The succinimide dispersant may be a derivative of a polyether amine or polyether polyamine. Typical polyether amine compounds contain at least one ether unit and will be chain terminated with at least one amine moiety. The polyether polyamines can be based on polymers derived from C2-C6 epoxides such as ethylene oxide, propylene oxide, and butylene oxide. Examples of polyether polyamines are sold under the Jeffamine® brand and are commercially available from Hunstman Corporation located in Houston, Tex.

In one embodiment the dispersant may be a polyolefin succinic acid ester, amide, or ester-amide. For instance, a polyolefin succinic acid ester may be a polyisobutylene succinic acid ester of pentaerythritol, or mixtures thereof. A polyolefin succinic acid ester-amide may be a polyisobutylene succinic acid reacted with an alcohol (such as pentaerythritol) and an amine (such as a diamine, typically diethyleneamine).

The dispersant may be an N-substituted long chain alkenyl succinimide. An example of an N-substituted long chain alkenyl succinimide may be polyisobutylene succinimide. Typically the polyisobutylene from which polyisobutylene succinic anhydride may be derived has a number average molecular weight of 350 to 5000, or 550 to 3000 or 750 to 2500. Succinimide dispersants and their preparation are disclosed, for instance in U.S. Pat. Nos. 3,172,892, 3,219,666, 3,316,177, 3,340,281, 3,351,552, 3,381,022, 3,433,744, 3,444,170, 3,467,668, 3,501,405, 3,542,680, 3,576,743, 3,632,511, 4,234,435, Re 26,433, and U.S. Pat. Nos. 6,165,235, 7,238,650 and EP Patent Application 0 355 895 A.

The dispersants may also be post-treated by conventional methods by a reaction with any of a variety of agents. Among these are boron compounds (such as boric acid), urea, thiourea, dimercaptothiadiazoles, carbon disulfide, aldehydes, ketones, carboxylic acids such as terephthalic acid, hydrocarbon-substituted succinic anhydrides, maleic anhydride, nitriles, epoxides, and phosphorus compounds. In one embodiment the post-treated dispersant may be borated. In one embodiment the post-treated dispersant may be reacted with dimercaptothiadiazoles. In one embodiment the post-treated dispersant may be reacted with phosphoric or phosphorous acid. In one embodiment the post-treated dispersant may be reacted with terephthalic acid and boric acid (as described in US Patent Application US2009/0054278.

In one embodiment the dispersant may be borated or non-borated. Typically a borated dispersant may be a succinimide dispersant. In one embodiment, the ashless dispersant may be boron-containing, i.e., has incorporated boron and delivers said boron to the lubricant composition. The boron-containing dispersant may be present in an amount to deliver at least 25 ppm boron, at least 50 ppm boron, or at least 100 ppm boron to the lubricant composition. In one embodiment, the lubricant composition may be free of a boron-containing dispersant, i.e. delivers no more than 10 ppm boron to the final formulation.

Dispersants may be derived from, as the polyolefin, high vinylidene polyisobutylene, that is, having greater than 50, 70, or 75% terminal vinylidene groups (α and β isomers). In certain embodiments, the succinimide dispersant may be prepared by the direct alkylation route. In other embodiments it may comprise a mixture of direct alkylation and chlorine-route dispersants. The dispersant may be prepared/obtained/obtainable from reaction of succinic anhydride by an "ene" or "thermal" reaction, by what is referred to as a "direct alkylation process". The "ene" reaction mechanism and general reaction conditions are summarised in "Maleic Anhydride", pages 147-149, Edited by B. C. Trivedi and B. C. Culbertson and Published by Plenum Press in 1982. The dispersant prepared by a process that includes an "ene" reaction may be a polyisobutylene succinimide having a carbocyclic ring present on less than 50 mole %, or 0 to less than 30 mole %, or 0 to less than 20 mole %, or 0 mole % of the dispersant molecules. The "ene" reaction may have a reaction temperature of 180° C. to less than 300° C., or 200° C. to 250° C., or 200° C. to 220° C.

The dispersant may also be obtained/obtainable from a chlorine-assisted process, often involving Diels-Alder chemistry, leading to formation of carbocyclic linkages. The process is known to a person skilled in the art. The chlorine-assisted process may produce a dispersant that may be a polyisobutylene succinimide having a carbocyclic ring present on 50 mole % or more, or 60 to 100 mole % of the dispersant molecules. Both the thermal and chlorine-assisted processes are described in greater detail in U.S. Pat. No. 7,615,521, columns 4-5 and preparative examples A and B.

The dispersant may have a carbonyl to nitrogen ratio (CO:N ratio) of 5:1 to 1:10, 2:1 to 1:10, or 2:1 to 1:5, or 2:1 to 1:2. In one embodiment the dispersant may have a CO:N ratio of 2:1 to 1:10, or 2:1 to 1:5, or 2:1 to 1:2, or 1:1.4 to 1:0.6.

The dispersant may be present at 0 wt % to 20 wt %, 0.1 wt % to 15 wt %, or 0.5 wt % to 9 wt %, or 1 wt % to 8.5 wt % of the lubricating composition.

In one embodiment the lubricating composition may be a lubricating composition further comprising a molybdenum compound. The molybdenum compound may be an antiwear agent or an antioxidant. The molybdenum compound may be chosen from of molybdenum dialkyldithiophosphates, molybdenum dithiocarbamates, amine salts of molybdenum compounds, and mixtures thereof. The molybdenum compound may provide the lubricating composition with 0 to 1000 ppm, or 5 to 1000 ppm, or 10 to 750 ppm, 5 ppm to 300 ppm, or 20 ppm to 250 ppm of molybdenum.

Antioxidants include sulfurised olefins, diarylamines, alkylated diarylamines, hindered phenols, molybdenum compounds (such as molybdenum dithiocarbamates), hydroxyl thioethers, or mixtures thereof. In one embodiment the lubricating composition includes an antioxidant, or mixtures thereof. The antioxidant may be present at 0 wt % to 15 wt %, or 0.1 wt % to 10 wt %, or 0.5 wt % to 5 wt %, or 0.5 wt % to 3 wt %, or 0.3 wt % to 1.5 wt % of the lubricating composition.

The diarylamine or alkylated diarylamine may be a phenyl-α-naphthylamine (PANA), an alkylated diphenylamine, or an alkylated phenylnapthylamine, or mixtures thereof. The alkylated diphenylamine may include di-nonylated diphenylamine, nonyl diphenylamine, octyl diphenylamine, di-octylated diphenylamine, di-decylated diphenylamine, decyl diphenylamine and mixtures thereof. In one embodiment the diphenylamine may include nonyl diphenylamine, dinonyl diphenylamine, octyl diphenylamine, dioctyl diphenylamine, or mixtures thereof. In one embodiment the alkylated diphenylamine may include nonyl diphenylamine, or dinonyl diphenylamine. The alkylated diarylamine may include octyl, di-octyl, nonyl, di-nonyl, decyl or di-decyl phenylnapthylamines.

The hindered phenol antioxidant often contains a secondary butyl and/or a tertiary butyl group as a sterically hindering group. The phenol group may be further substituted with a hydrocarbyl group (typically linear or branched alkyl) and/or a bridging group linking to a second aromatic group. Examples of suitable hindered phenol antioxidants include 2,6-di-tert-butylphenol, 4-methyl-2,6-di-tert-butylphenol, 4-ethyl-2,6-di-tert-butylphenol, 4-propyl-2,6-di-tert-butylphenol or 4-butyl-2,6-di-tert-butylphenol, or 4-dodecyl-2,6-di-tert-butylphenol. In one embodiment the hindered phenol antioxidant may be an ester and may include, e.g., Irganox™ L-135 from Ciba. A more detailed description of suitable ester-containing hindered phenol antioxidant chemistry is found in U.S. Pat. No. 6,559,105.

Examples of molybdenum dithiocarbamates, which may be used as an antioxidant, include commercial materials sold under the trade names such as Vanlube 822™ and Molyvan™ A from R. T. Vanderbilt Co., Ltd., and Adeka Sakura-Lube™ S-100, S-165, S-600 and 525, or mixtures thereof.

In one embodiment the lubricating composition further includes a viscosity modifier. The viscosity modifier is known in the art and may include hydrogenated styrene-butadiene rubbers, ethylene-propylene copolymers, polymethacrylates, polyacrylates, hydrogenated styrene-isoprene polymers, hydrogenated diene polymers, polyalkyl styrenes, polyolefins, esters of maleic anhydride-olefin copolymers (such as those described in International Application WO 2010/014655), esters of maleic anhydride-styrene copolymers, or mixtures thereof.

The dispersant viscosity modifier may include functionalised polyolefins, for example, ethylene-propylene copolymers that have been functionalised with an acylating agent such as maleic anhydride and an amine; polymethacrylates functionalised with an amine, or styrene-maleic anhydride copolymers reacted with an amine. More detailed description of dispersant viscosity modifiers are disclosed in International Publication WO2006/015130 or U.S. Pat. Nos. 4,863,623; 6,107,257; 6,107,258; 6,117,825; and 7,790,661. In one embodiment the dispersant viscosity modifier may include those described in U.S. Pat. No. 4,863,623 (see column 2, line 15 to column 3, line 52) or in International Publication WO2006/015130 (see page 2, paragraph [0008] and preparative examples are described. In one embodiment the dispersant viscosity modifier may include those described in U.S. Pat. No. 7,790,661 column 2, line 48 to column 10, line 38.

In one embodiment the lubricating composition of the disclosed technology further comprises a dispersant viscosity modifier. The dispersant viscosity modifier may be present at 0 wt % to 5 wt %, or 0 wt % to 4 wt %, or 0.05 wt % to 2 wt %, or 0.2 wt % to 1.2 wt % of the lubricating composition.

In one embodiment the friction modifier may be chosen from of long chain fatty acid derivatives of amines, long chain fatty esters, or derivatives of long chain fatty epoxides; fatty imidazolines; amine salts of alkylphosphoric acids; fatty alkyl tartrates; fatty alkyl tartrimides; fatty alkyl tartramides; fatty glycolates; and fatty glycolamides. The friction modifier may be present at 0 wt % to 6 wt %, or 0.01 wt % to 4 wt %, or 0.05 wt % to 2 wt %, or 0.1 wt % to 2 wt % of the lubricating composition.

As used herein the term "fatty alkyl" or "fatty" in relation to friction modifiers means a carbon chain having 10 to 22 carbon atoms, typically a straight carbon chain.

Examples of suitable friction modifiers include long chain fatty acid derivatives of amines, fatty esters, or fatty epoxides; fatty imidazolines such as condensation products of carboxylic acids and polyalkylene-polyamines; amine salts of alkylphosphoric acids; fatty alkyl tartrates; fatty alkyl tartrimides; fatty alkyl tartramides; fatty phosphonates; fatty phosphites; borated phospholipids, borated fatty epoxides; glycerol esters; borated glycerol esters; fatty amines; alkoxylated fatty amines; borated alkoxylated fatty amines; hydroxyl and polyhydroxy fatty amines including tertiary hydroxy fatty amines; hydroxy alkyl amides; metal salts of fatty acids; metal salts of alkyl salicylates; fatty oxazolines; fatty ethoxylated alcohols; condensation products of carboxylic acids and polyalkylene polyamines; or reaction products from fatty carboxylic acids with guanidine, aminoguanidine, urea, or thiourea and salts thereof.

Friction modifiers may also encompass materials such as sulfurised fatty compounds and olefins, molybdenum dialkyldithiophosphates, molybdenum dithiocarbamates, sunflower oil or soybean oil monoester of a polyol and an aliphatic carboxylic acid.

In one embodiment the friction modifier may be a long chain fatty acid ester. In another embodiment the long chain fatty acid ester may be a mono-ester and in another embodiment the long chain fatty acid ester may be a triglyceride.

The lubricating composition optionally further includes at least one antiwear agent. Examples of suitable antiwear agents include titanium compounds, tartaric acid derivatives such as tartrate esters, amides or tartrimides, oil soluble amine salts of phosphorus compounds, sulfurised olefins, metal dihydrocarbyldithiophosphates (such as zinc dialkyldithiophosphates), phosphites (such as dibutyl phosphite), phosphonates, thiocarbamate-containing compounds, such as thiocarbamate esters, thiocarbamate amides, thiocarbamic ethers, alkylene-coupled thiocarbamates, and bis(S-alkyldithiocarbamyl) disulfides.

The antiwear agent may in one embodiment include a tartrate or tartrimide as disclosed in International Publication WO 2006/044411 or Canadian Patent CA 1 183 125. The tartrate or tartrimide may contain alkyl-ester groups, where the sum of carbon atoms on the alkyl groups may be at least 8. The antiwear agent may in one embodiment include a citrate as is disclosed in US Patent Application 2005/0198894.

The lubricating composition may further include a phosphorus-containing antiwear agent. Typically the phosphorus-containing antiwear agent may be a zinc dialkyldithiophosphate, phosphite, phosphate, phosphonate, and ammonium phosphate salts, or mixtures thereof. Zinc dialkyldithiophosphates are known in the art. The antiwear agent may be present at 0 wt % to 3 wt %, or 0.1 wt % to 1.5 wt %, or 0.5 wt % to 0.9 wt % of the lubricating composition.

Another class of additives includes oil-soluble titanium compounds as disclosed in U.S. Pat. No. 7,727,943 and US2006/0014651. The oil-soluble titanium compounds may function as antiwear agents, friction modifiers, antioxidants, deposit control additives, or more than one of these functions. In one embodiment the oil soluble titanium compound may be a titanium (IV) alkoxide. The titanium alkoxide may be formed from a monohydric alcohol, a polyol or mixtures thereof. The monohydric alkoxides may have 2 to 16, or 3 to 10 carbon atoms. In one embodiment, the titanium alkoxide may be titanium (IV) isopropoxide. In one embodiment, the titanium alkoxide may be titanium (IV) 2-ethylhexoxide. In one embodiment, the titanium compound comprises the alkoxide of a vicinal 1,2-diol or polyol. In one embodiment, the 1,2-vicinal diol comprises a fatty acid mono-ester of glycerol, often the fatty acid may be oleic acid.

In one embodiment, the oil soluble titanium compound may be a titanium carboxylate. In one embodiment the titanium (IV) carboxylate may be titanium neodecanoate.

Foam inhibitors that may be useful in the compositions of the disclosed technology include polysiloxanes, copolymers of ethyl acrylate and 2-ethylhexyl-acrylate and optionally vinyl acetate; demulsifiers including fluorinated polysiloxanes, trialkyl phosphates, polyethylene glycols, polyethylene oxides, polypropylene oxides and (ethylene oxide-propylene oxide) polymers.

Pour point depressants that may be useful in the compositions of the disclosed technology include polyalphaolefins, esters of maleic anhydride-styrene copolymers, poly(meth)acrylates, polyacrylates or polyacrylamides.

Demulsifiers include trialkyl phosphates, and various polymers and copolymers of ethylene glycol, ethylene oxide, propylene oxide, or mixtures thereof different from the non-hydroxy terminated acylated polyalkylene oxide of the disclosed technology.

Metal deactivators include derivatives of benzotriazoles (typically tolyltriazole), 1,2,4-triazoles, benzimidazoles, 2-alkyldithiobenzimidazoles or 2-alkyldithiobenzothiazoles. The metal deactivators may also be described as corrosion inhibitors.

Seal swell agents include sulpholene derivatives Exxon Necton37™ (FN 1380) and Exxon Mineral Seal Oil™ (FN 3200).

An engine lubricating composition in different embodiments may have a composition as disclosed in the following table:

| | Embodiments (wt %) | | |
|---|---|---|---|
| Additive | A | B | C |
| oxyalkylated aromatic polyol compound | 0.01 to 5 | 0.05 to 3 | 0.1 to 1.5 |
| Overbased Detergent | 2 to 9 | 3 to 8 | 3 to 5 |
| Dispersant Viscosity Modifier | 0 to 5 | 0 to 4 | 0.05 to 2 |
| Dispersant | 0 to 12 | 0 to 8 | 0.5 to 6 |
| Antioxidant | 0.1 to 13 | 0.1 to 10 | 0.5 to 5 |
| Antiwear Agent | 0.1 to 15 | 0.1 to 10 | 0.3 to 5 |
| Friction Modifier | 0.01 to 6 | 0.05 to 4 | 0.1 to 2 |
| Viscosity Modifier | 0 to 10 | 0.5 to 8 | 1 to 6 |
| Any Other Performance Additive | 0 to 10 | 0 to 8 | 0 to 6 |
| Oil of Lubricating Viscosity | Balance to 100% | Balance to 100% | Balance to 100% |

Industrial Application

In one embodiment the disclosed technology provides a method of lubricating an internal combustion engine. The engine components may have a surface of steel or aluminum.

An aluminum surface may be derived from an aluminum alloy that may be a eutectic or a hyper-eutectic aluminum alloy (such as those derived from aluminum silicates, aluminum oxides, or other ceramic materials). The aluminum surface may be present on a cylinder bore, cylinder block, or piston ring having an aluminum alloy, or aluminum composite.

The internal combustion engine may or may not have an exhaust gas recirculation system. The internal combustion engine may be fitted with an emission control system or a turbocharger. Examples of the emission control system include diesel particulate filters (DPF), or systems employing selective catalytic reduction (SCR).

In one embodiment the internal combustion engine may be a diesel fuelled engine (typically a heavy duty diesel engine), a gasoline fuelled engine, a natural gas fuelled engine, a mixed gasoline/alcohol fuelled engine, or a hydrogen fuelled internal combustion engine. In one embodiment the internal combustion engine may be a diesel fuelled engine and in another embodiment a gasoline fuelled engine. Diesel fueled engines may be fueled with a mixture of conventional diesel fuel and bio-derived diesel fuel (i.e. bio-diesel). In one embodiment the diesel engine fuel may comprise 5 volume percent to 100 volume percent bio-diesel (i.e. B5 to b100); in one embodiment the diesel fuel comprises 5 volume percent to 50 volume percent bio-diesel or 8 volume percent to 30 volume percent bio-diesel. In one embodiment the diesel fuel may be substantially free of (i.e. contains less than 1 volume percent) bio-diesel. In one embodiment the internal combustion engine may be a heavy duty diesel engine. In one embodiment, the internal combustion engine may be a gasoline direct injection (GDI) engine. When the internal combustion engine may be a gasoline engine, and the oxyalkylated group of the oxyalkylated aromatic polyol compound of the disclosed technology has formula —$(R^1O)_n$—, wherein $R^1$ may be ethylene, propylene, butylene group, or mixtures thereof, with the proviso that if $R^1$ comprises ethylene groups the resultant oxyalkylated aromatic polyol compound may be a random or block copolymer derived from ethylene glycol and either (i) propylene glycol or (ii) butylene glycol; and n may be independently from 1 to 50, or 1 to 20.

The internal combustion engine may be a 2-stroke or 4-stroke engine. Suitable internal combustion engines include marine diesel engines, aviation piston engines, low-load diesel engines, and automobile and truck engines. The marine diesel engine may be lubricated with a marine diesel cylinder lubricant (typically in a 2-stroke engine), a system oil (typically in a 2-stroke engine), or a crankcase lubricant (typically in a 4-stroke engine). In one embodiment the internal combustion engine may be a 4-stroke engine, and may be a compression ignition engine or a positive ignition natural gas (NG) or LPG engine.

The lubricant composition for an internal combustion engine may be suitable for any engine lubricant irrespective of the sulfur, phosphorus or sulphated ash (ASTM D-874) content. The sulfur content of the engine oil lubricant may be 1 wt % or less, or 0.8 wt % or less, or 0.5 wt % or less, or 0.3 wt % or less. In one embodiment the sulfur content may be in the range of 0.001 wt % to 0.5 wt %, or 0.01 wt % to 0.3 wt %. The phosphorus content may be 0.2 wt % or less, or 0.12 wt % or less, or 0.1 wt % or less, or 0.085 wt % or less, or 0.08 wt % or less, or even 0.06 wt % or less, 0.055 wt % or less, or 0.05 wt % or less. In one embodiment the phosphorus content may be 0.04 wt % to 0.12 wt %. In one embodiment the phosphorus content may be 100 ppm to 1000 ppm, or 200 ppm to 600 ppm. The total sulphated ash content may be 0.3 wt % to 1.2 wt %, or 0.5 wt % to 1.2 wt % or 1.1 wt % of the lubricating composition. In one embodiment the sulphated ash content may be 0.5 wt % to 1.2 wt % of the lubricating composition. The TBN (as measured by ASTM D2896) of the engine oil lubricant may be 5 mg KOH/g to 15 mg KOH/g, or 6 mg KOH/g to 12 mg KOH/g, or 7 mg KOH/g to 10 mg KOH/g.

In one embodiment the lubricating composition may be an engine oil, wherein the lubricating composition may be characterised as having at least one of (i) a sulfur content of 0.5 wt % or less, (ii) a phosphorus content of 0.12 wt % or less, and (iii) a sulphated ash content of 0.5 wt % to 1.1 wt % of the lubricating composition.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include: hydrocarbon substituents, including aliphatic, alicyclic, and aromatic substituents; substituted hydrocarbon substituents, that is, substituents containing non-hydrocarbon groups which, in the context of this disclosed technology, do not alter the predominantly hydrocarbon nature of the substituent; and hetero substituents, that is, substituents which similarly have a predominantly hydrocarbon character but contain other than carbon in a ring or chain. A more detailed definition of the term "hydrocarbyl substituent" or "hydrocarbyl group" is described in International Publication WO2008147704, or a similar definition in published application US 2010-0197536.

The following examples provide illustrations of the disclosed technology. These examples are non-exhaustive and are not intended to limit the scope of the disclosed technology.

EXAMPLES

Inventive Preparative Example A

Catechol (143.1 g) is charged to a 1 L 4 neck round bottom flask equipped with a condenser, thermocouple, and addition funnel under a nitrogen blanket. The catechol is warmed to 110° C. until it flows. Potassium hydroxide (3.65 g) is then added in 1 portion and an exotherm is observed (max temperature of 165° C.). 2-tetradecyloxirane (350 g) is then added over 30 minutes; another exotherm is observed (180° C.). The reaction temperature is held at 155° C. for 6 hours, after which the reaction mixture is quenched in deionized water at ambient temperature. After cooling to room temperature, the product is isolated by filtration to give a waxy orange solid.

Inventive Preparative Example C (Alkylation of Oxyalkylated Catechol)

The product of Example A (72 g), toluene (60 g), and Amberlyst 15 (6.9 g) are charged to a 500 mL flask with overhead stirring, an addition funnel, and a reflux condenser under a nitrogen blanket (0.5 scfh). The reaction mixture is heated to 110° C. and dodec-1-ene (34.6 g) is added dropwise over 30 minutes. The red-brown solution is refluxed for 7 hours, filtered, and the toluene is removed under vacuum to give the red oily product.

Inventive Preparative Example E (Oxyalkylation of Alkylated Catechol)

Catechol (308.8 g), and heptane (300 mL) are charged to a 4 neck 3 L vessel equipped with an overhead stirrer w/paddle, thermowell, reflux condenser, and addition funnel under nitrogen blanket. The temperature is increased to 100° C., and Amberlyst 15 catalyst (30 g) is added over 10 minutes. Dodec-1-ene (300 g) is charged to the addition funnel and added dropwise over 1 hour. The orange reaction mixture is held at 100° C. for 3 hours and then cooled to ambient temperature during which time the alkylated catechol product separated from solution. The product is isolated by filtration to give an orange solid. The solid alkylated catechol product (232 g) is charged to a 5 L round bottom flask equipped with a reflux condenser, overhead mechanical stirrer with paddle, thermowell, and addition funnel. Toluene (2 L) and sodium hydroxide (3.31 g) are added to the reaction mixture which is held at 50° C. 1,2-epoxybutane (72.63 g) is dissolved in toluene (400 mL) and charged to the addition funnel. The epoxide solution is added dropwise over 2 hours. The reaction mixture is maintained at 50° C. for 24 hours, after which it is quenched in aqueous HCL (600 mL, 10% in water), dried, and purified under vacuum to yield a dark red oily product.

Various inventive examples of oxyalkylated catechols are prepared in analogous fashion to the examples above utilizing the appropriate epoxides; preparative catechol examples are summarized in Table 1.

TABLE 1

Examples of Oxyalkylated Catechols

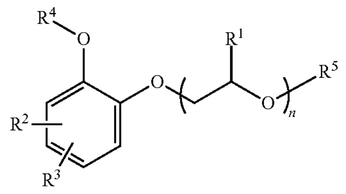

| | $R^1$ | $R^2$ | $R^3$ | $R^4$ | $R^5$ | n |
|---|---|---|---|---|---|---|
| Ex A | $C_{10}H_{25}$ | H | H | H | H | 1 |
| Ex B | $C_{10}H_{25}$ | H | H | H | H | 1 |

TABLE 1-continued

Examples of Oxyalkylated Catechols

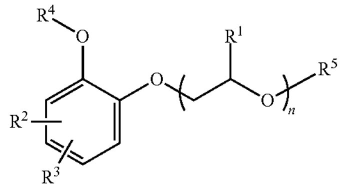

| | $R^1$ | $R^2$ | $R^3$ | $R^4$ | $R^5$ | n |
|---|---|---|---|---|---|---|
| Ex C | $C_{14}H_{29}$ | $C_{12}H_{25}$ | H | H | H | 1 |
| Ex D | $C_{10}H_{25}$ | $C_{12}H_{25}$ | H | H | H | 1 |
| Ex E | $C_2H_5$ | $C_{12}H_{25}$ | H | H | H | 1 |
| Ex F | $C_2H_5$ | $C_{12}H_{25}$ | $C_{12}H_{25}$ | H | H | 1 |
| Ex G | $C_2H_5$ | $C_{12}H_{25}$ | H | $—CH_2CH(OH)C_2H_5$ | H | 1 |
| Ex H | $C_2H_5$ | $C_{20}$-$C_{24}$ | H | H | H | 1 |
| Ex N | —O($C_{12-14}$ alkyl) | H | H | H | H | 1 |

Example J

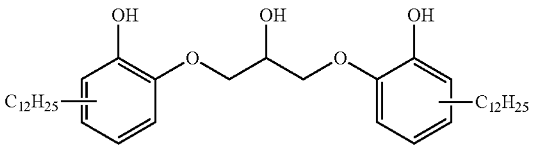

Example K

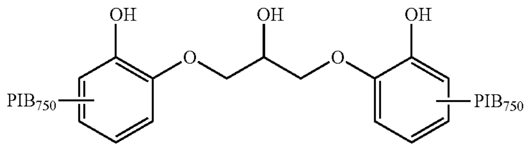

Inventive examples of various oxyalkylated gallols are summarized below (Examples L and M):

Example L

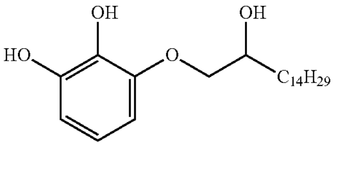

Example M

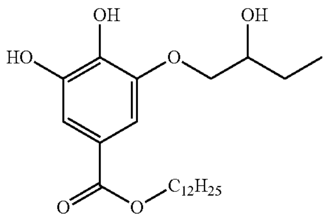

Inventive Preparative Example N: Catechol (110 g) is charged to a 4 neck 2 L vessel equipped with an overhead stirrer w/paddle, thermowell, reflux condenser, and addition funnel under nitrogen blanket. The reaction mixture is heated to 95° C. and potassium hydroxide (56.1 g) is added in one portion. A mixture of dodecyl- and tetradecyl glycidyl ether (281.7 g) is added dropwide to the reaction mixture over 2 hours, and the subsequent reaction mixture is heated to 140° C. and held there for 4 hours. The product mixture is washed with water, extracted with hexanes, and dried to produce a dark red liquid (665 g).

A series of 5W-40 engine lubricants suitable for use in light duty diesel engines are prepared in Group III base oil of lubricating viscosity containing the additives described above as well as conventional additives including polymeric viscosity modifier, ashless succinimide dispersant, overbased detergents, antioxidants (combination of phenolic ester, diarylamine, and sulfurized olefin), zinc dialkyldithiophosphate (ZDDP), as well as other performance additives as follows (Table 2 and 3).

TABLE 2

| Lubricating Compositions | | | | | | | | |
|---|---|---|---|---|---|---|---|---|
| | CEX | EX1 | EX2 | EX3 | EX4 | EX5 | EX6 | |
| Base Oil | Balance to 100% | | | | | | | |
| Example A | | 1 | | | | | | |
| Example B | | | 1 | | | | | |
| Example C | | | | 1 | | | | |
| Example D | | | | | 1 | | | |
| Example E | | | | | | 1 | | |
| Example F | | | | | | | 1 | |
| Example N | | | | | | | | 1 |
| Calcium Sulfonate[1] | 0.06 | 0.06 | 0.06 | 0.06 | 0.06 | 0.06 | 0.06 | 0.06 |
| Calcium Phenate[2] | 1.45 | 1.45 | 1.45 | 1.45 | 1.45 | 1.45 | 1.45 | 1.45 |
| ZDDP[3] | 0.5 | 0.5 | 0.5 | 0.5 | 0.5 | 0.5 | 0.5 | 0.5 |
| Antioxidant[4] | 2 | 2 | 2 | 2 | 2 | 2 | 2 | 2 |
| Dispersant[5] | 4.9 | 4.9 | 4.9 | 4.9 | 4.9 | 4.9 | 4.9 | 4.9 |
| Viscosity Modifier[6] | 1.23 | 1.23 | 1.23 | 1.23 | 1.23 | 1.23 | 1.23 | 1.23 |
| Additional additives[7] | 0.36 | 0.36 | 0.36 | 0.36 | 0.36 | 0.36 | 0.36 | 0.36 |
| % Phos | 0.045 | 0.045 | 0.045 | 0.045 | 0.045 | 0.045 | 0.045 | 0.045 |
| % Sulfur | 0.18 | 0.18 | 0.18 | 0.18 | 0.18 | 0.18 | 0.18 | 0.18 |

[1]Overbased calcium alkylbenzene sulfonate detergent with TBN from 200-600

[2]Overbased calcium sulfur-coupled phenate detergent

[3]Secondary ZDDP derived from mixture of C3 and C6 alcohols

[4]Combination of phenolic and arylamine antioxidants

[5]Succinimide dispersant derived from polyisobutylene

[6]Styrene-diene block copolymer

[7]Additional additives include friction modifier, anti-foam agents, and pour point depressants

TABLE 3

| Lubricating Compositions | | | |
|---|---|---|---|
| | BL2 | EX7 | EX8 |
| Base Oil | Balance to 100% | | |
| Example E | | 1 | |
| Example F | | | 1 |
| Calcium Detergents[1] | 1.29 | 1.29 | 1.29 |
| ZDDP[2] | 0.86 | 0.86 | 0.86 |
| Antioxidant[3] | 3.2 | 3.2 | 3.2 |
| Dispersant[4] | 4.97 | 4.97 | 4.97 |
| Viscosity Modifier[5] | 1.44 | 1.44 | 1.44 |
| Additional additives[6] | 0.46 | 0.46 | 0.46 |
| % Phosphorus | 0.077 | 0.077 | 0.077 |
| % Sulfur | 0.25 | 0.25 | 0.25 |

[1]Mixture of overbased calcium sulfonate and calcium phenate detergents

[2]Secondary ZDDP derived from mixture of C3 and C6 alcohols

[3]Combination of phenolic and arylamine antioxidants

[4]Succinimide dispersant derived from polyisobutylene

[5]Styrene-diene block copolymer

[6]Additional additives include friction modifier, anti-foam agents, and pourpoint depressants A 5W-30 formulation is prepared with the additives described above as well as conventional additives including polymeric viscosity modifier, ashless succinimide dispersant, overbased detergents, antioxidants (combination of phenolic ester, diarylamine, and sulfurized olefin), zinc dialkyldithiophosphate (ZDDP), as well as other performance additives as follows (Table 4).

TABLE 4

| Lubricating Compositions | | |
|---|---|---|
| | BL3 | EX9 |
| Group III Base Oil | Balance to 100% | |
| Example A | 0 | 1.26 |
| Calcium Sulfonate[1] | 0.06 | 0.06 |
| ZDDP[2] | 0.46 | 0.46 |
| Antioxidant[3] | 2.0 | 2.0 |
| Dispersant[4] | 4.9 | 4.9 |
| Viscosity Modifier[5] | 1.23 | 1.23 |
| Additional additives[6] | 0.41 | 0.41 |
| % Phosphorus | 0.045 | 0.045 |
| % Sulfur | 0.095 | 0.095 |

[1]Overbased calcium alkylbenzene sulfonate (690 TBN, oil free)

[2]Secondary zinc dialkyldithiophosphate derived from C3/C6 alcohols

[3]Combination of diarylamine and hindered phenol antioxidants

[4]PIBsuccinimide dispersant derived from high vinylidene PIB (18 TBN)

[5]Styrene butadiene block copolymer

[6]Additional additives include friction modifiers, corrosion inhibitors, foam inhibitors, and pourpoint depressants A 15W-40 diesel formulation is prepared with the additives described above as well as conventional additives including polymeric viscosity modifier, ashless succinimide dispersant, overbased detergents, antioxidants (combination of phenolic ester, diarylamine, and sulfurized olefin), zinc dialkyldithiophosphate (ZDDP), as well as other performance additives as follows (Table 5).

TABLE 5

| Lubricating Compositions | | |
|---|---|---|
| | BL4 | EX10 |
| Group II Base Oil | Balance to 100% | |
| Example A | 0 | 0.6 |
| Calcium Sulfonate[1] | 0.9 | 0.9 |
| ZDDP[2] | 1.0 | 1.0 |
| Antioxidant[3] | 1.23 | 1.23 |
| Dispersant[4] | 4.1 | 4.1 |

TABLE 5-continued

| Lubricating Compositions | | |
|---|---|---|
| | BL4 | EX10 |
| Viscosity Modifier[5] | 0.56 | 0.56 |
| Additional additives[6] | 0.82 | 0.82 |
| % Phosphorus | 0.11 | 0.11 |
| % Sulfur | 0.32 | 0.32 |

[1]Mixture of overbased calcium alkylbenzene sulfonates
[2]Secondary zinc dialkyldithiophosphate derived from C3/C6 alcohols
[3]Combination of sulfurized olefin, diarylamine, and hindered phenol antioxidants
[4]Conventional PIBsuccinimide dispersant (57 TBN)
[5]Ethylene-propylene copolymer
[6]Additional additives include corrosion inhibitors, foam inhibitors, and pourpoint depressants The formulations are evaluated in both bench oxidation-deposit tests as well as a fired engine test designed to evaluate deposit control of lubricants.

The lubricating compositions are tested in a Panel Coker heated to 325° C., with a sump temperature of 105° C., and a splash/bake cycle of 120 s/45 s. The airflow is 350 ml/min, with a spindle speed of 1000 rpm and the test lasts for 4 hours. The oil is splashed onto an aluminum panel which is then optically rated by computer. Performance ranges from 0% (black panel) to 100% (clean panel).

Each example is evaluated in the hot Tube deposit test. Approximately 4 ml of oil being pumped through a 1 mm bore, 265 mm length of glass tube over a 16 hour test period at 305° C. Flow is aided by the use of 10 ml/min. of air.

Each example is evaluated in the Komatsu Hot Tube Test. The Komatsu Hot Tube Test evaluates the high temperature stability of a lubricating composition. Oil droplets are pushed up by air inside a heated narrow glass capillary tube and the thin film oxidative stability of a lubricant is measured. A rating of 0 refers to heavy deposit formation and a rating of 10 means a clean glass tube at the end of the test. The test is run at 320° C. and is described in SAE paper 840262.

Each sample is evaluted using ASTM D6335-98, the standard test method for determination of high temperature deposits by thermo-oxidation of engine oils in a simulation test. The procedure determines the amount of deposits formed by automotive engine oils utilizing the thermo-oxidation engine oil simulation test (TEOST).

The lubricating compositions are also evaluated in the Sequence IIIG engine test following the test procedure of ASTM D7320-14 (entitled Standard Test Method for Evaluation of Automotive Engine Oils in the Sequence IIIG, spark-ignition engine). The test measures oxidation, and weighted piston deposits (WPD). Typically better results are obtained for samples having a higher rating.

The lubricating compositions are also evaluated in the Volkswagen (VW) TDI engine test. The test procedure follows the PV1452 and CEC L-78-T-99 methods as laid out in the ACEA oil sequences. This engine test rates lubricants on piston cleanliness (merit) and ring sticking.

TABLE 6

| Performance/Bench Test Data | | |
|---|---|---|
| | EX9 | EX10 |
| Hot Tube Test | | |
| Temperature (° C.) | 280 | 280 |
| Rating | 6 | 3 |

TABLE 6-continued

| Performance/Bench Test Data | | |
|---|---|---|
| | EX9 | EX10 |
| L-85-99 ACEA PDSC | | |
| Oxidation induction time (min) | 102 | 93 |
| Panel Coker | | |
| Rating | 60 | 59 |

The results obtained indicate that the oxyalkylated aromatic polyol compound significantly outperformed the baseline formulation in terms of deposit control capability.

The disclosed technology is capable of at least one of (i) control of fuel economy, (ii) control of corrosion, (iii) cleanliness (typically control of deposits, typically control/reduction of soot), and (iv) control of bore wear, typically in a passenger car internal combustion engine.

It is known that some of the materials described above may interact in the final formulation, so that the components of the final formulation may be different from those that are initially added. The products formed thereby, including the products formed upon employing lubricant composition of the disclosed technology in its intended use, may not be susceptible of easy description. Nevertheless, all such modifications and reaction products are included within the scope of the disclosed technology; the disclosed technology encompasses lubricant composition prepared by admixing the components described above.

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about". Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil, which may be customarily present in the commercial material, unless otherwise indicated. It is to be understood that the upper and lower amount, range, and ratio limits set forth herein may be independently combined. Similarly, the ranges and amounts for each element of the disclosed technology may be used together with ranges or amounts for any of the other elements.

While the disclosed technology has been explained in relation to its preferred embodiments, it is to be understood that various modifications thereof will become apparent to those skilled in the art upon reading the specification. Therefore, it is to be understood that the disclosed technology disclosed herein is intended to cover such modifications as fall within the scope of the appended claims.

What is claimed is:

1. A lubricating composition comprising an oil of lubricating viscosity and 0.01 wt % to 10 wt % of an oxyalkylated aromatic polyol compound represented by the formula:

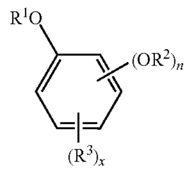

wherein $R^1$ is —$(CH_2CHR^5$—O—$)_mR^6$, $R^2$ is hydrogen, a hydrocarbyl group, or —(C═O)$R^4$, —$(CH_2CHR^5$—O—$)_mR^6$, n is 1 or 2, $R^3$ is a hydrocarbyl group, or —(C═O)O$R^4$, or —$(CH_2CHR^5$—O—$)_mR^6$, x is 1, $R^4$ is a hydrocarbyl group, $R^5$ is hydrogen or a hydrocarbyl group containing 1 to 32 carbon atoms, or $CH_2OR^8$, $R^6$ is hydrogen or a hydrocarbyl group, or —(C═O)$R^7$, $R^7$ is a hydrocarbyl group, $R^8$ is a hydrogen or a hydrocarbyl group containing 1 to 24 carbon atoms, and m=1 to 20.

2. The composition of claim 1, wherein $R^3$ is a polyisobutenyl or polyisobutylene group.

3. The composition of claim 1, wherein $R^3$ is an olefin group having 6 to 36 carbon atoms.

4. The composition of claim 1, wherein the oxyalkylated aromatic polyol compound is present in an amount ranging from 0.01 wt % to 5 wt % of the lubricating composition.

5. The composition of claim 1, further comprising an overbased detergent is chosen from of non-sulfur containing phenates, sulfur containing phenates, sulfonates, salixarates, salicylates, and mixtures thereof.

6. The composition of claim 5, wherein the overbased detergent is present at 3 wt % to 8 wt % of the lubricating composition.

7. The composition of claim 1, wherein the lubricating composition is characterised as having at least one of (i) a sulfur content of 0.2 wt % to 0.4 wt % or less, (ii) a phosphorus content of 0.08 wt % to 0.15 wt %, and (iii) a sulphated ash content of 0.5 wt % to 1.5 wt % or less.

8. The composition of claim 1, wherein the lubricating composition is characterized as having a total base number (TBN) content of at least 5 mg KOH/g.

9. A method of lubricating an internal combustion engine comprising supplying to the internal combustion engine a lubricating composition of claim 1.

10. The method of claim 9, wherein the internal combustion engine has a steel surface on a cylinder bore, a cylinder block, or a piston ring.

11. The method of claim 9, wherein the internal combustion engine is a heavy duty diesel internal combustion engine.

12. The method of claim 9, wherein the heavy duty diesel internal combustion engine has a technically permissible maximum laden mass over 3,500 kg, wherein the engine is a compression ignition engine or a positive ignition natural gas (NG) or LPG engine.

13. The method of claim 9, wherein the internal combustion engine is a passenger car internal combustion engine (typically a gasoline or diesel passenger car internal combustion engine).

* * * * *